(12) United States Patent
Bull et al.

(10) Patent No.: US 8,409,225 B2
(45) Date of Patent: Apr. 2, 2013

(54) TENDON REPAIR

(75) Inventors: Anthony Bull, London (GB); Adam Hill, London (GB)

(73) Assignee: Medical Device Innovations Limited (GB)

( * ) Notice: Subject to any disclaimer, the term of this patent is extended or adjusted under 35 U.S.C. 154(b) by 1114 days.

(21) Appl. No.: 12/298,013

(22) PCT Filed: Apr. 20, 2007

(86) PCT No.: PCT/GB2007/001442
§ 371 (c)(1),
(2), (4) Date: Oct. 21, 2008

(87) PCT Pub. No.: WO2007/125279
PCT Pub. Date: Nov. 8, 2007

(65) Prior Publication Data
US 2009/0069846 A1 Mar. 12, 2009

(30) Foreign Application Priority Data
Apr. 21, 2006 (GB) .................................. 0607958.6

(51) Int. Cl.
*A61B 17/04* (2006.01)
*A61B 17/84* (2006.01)
(52) U.S. Cl. ........................................ 606/148; 606/300
(58) Field of Classification Search .................. 606/144, 606/148, 205, 139, 96, 228, 300, 232
See application file for complete search history.

(56) References Cited

U.S. PATENT DOCUMENTS

| | | | |
|---|---|---|---|
| 4,738,255 A | 4/1988 | Goble et al. | |
| 5,222,977 A | 6/1993 | Esser | |
| 5,312,412 A * | 5/1994 | Whipple | 606/96 |
| 5,330,468 A * | 7/1994 | Burkhart | 606/96 |
| 5,575,801 A | 11/1996 | Habermeyer et al. | |
| 5,584,839 A * | 12/1996 | Gieringer | 606/96 |
| 5,681,333 A * | 10/1997 | Burkhart et al. | 606/148 |
| RE36,020 E | 12/1998 | Moore et al. | |
| 5,980,538 A | 11/1999 | Fuchs et al. | |
| 6,013,083 A | 1/2000 | Bennett | |
| 6,117,144 A | 9/2000 | Nobles et al. | |
| 6,206,886 B1 | 3/2001 | Bennett | |
| 6,491,714 B1 | 12/2002 | Bennett | |
| 6,605,096 B1 | 8/2003 | Richart | |
| 7,569,059 B2 * | 8/2009 | Cerundolo | 606/86 R |
| 2001/0041916 A1 * | 11/2001 | Bonutti | 606/232 |
| 2003/0195528 A1 | 10/2003 | Ritchart | |

(Continued)

FOREIGN PATENT DOCUMENTS

| WO | 9522288 | 8/1995 |
|---|---|---|
| WO | 02065892 A2 | 8/2002 |

(Continued)

OTHER PUBLICATIONS

International Search Report: PCT/GB2007/001442, Dated: Oct. 8, 2007, (3 pages).

*Primary Examiner* — Corrine M McDermott
*Assistant Examiner* — Christina Lauer
(74) *Attorney, Agent, or Firm* — Brooks Kushman P.C.

(57) ABSTRACT

An assembly is described for repairing torn tendons by reattaching them to a bone, in particular although not exclusively for repairing a torn rotator cuff tendon, which allows for reduction of the gap between the tendon and the humerus by pushing the tendon onto its attachment site. Also described is a method of repairing a torn rotator cuff tendon by pushing it onto its attachment site and suturing through the humeral head.

22 Claims, 13 Drawing Sheets

U.S. PATENT DOCUMENTS

| | | |
|---|---|---|
| 2004/0193217 A1 | 9/2004 | Lubbers et al. |
| 2004/0236353 A1* | 11/2004 | Bain et al. ............ 606/139 |
| 2004/0243135 A1 | 12/2004 | Koseki |
| 2005/0085850 A1 | 4/2005 | Harris et al. |

FOREIGN PATENT DOCUMENTS

| | | |
|---|---|---|
| WO | 03034895 A2 | 5/2003 |
| WO | 2006009471 A1 | 1/2006 |

* cited by examiner

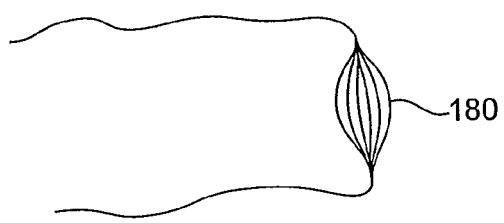
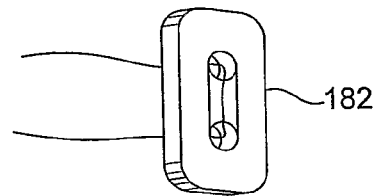
FIG. 24A　　　　　　FIG. 24B
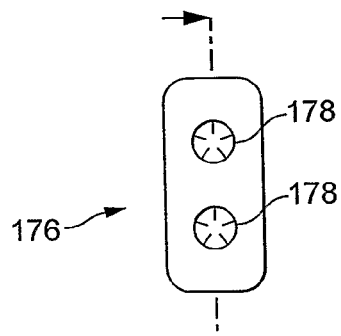
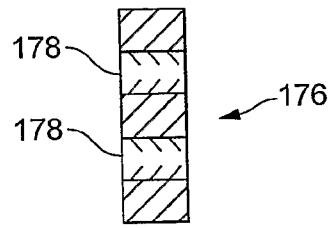
FIG. 25A　　　　　　FIG. 25B
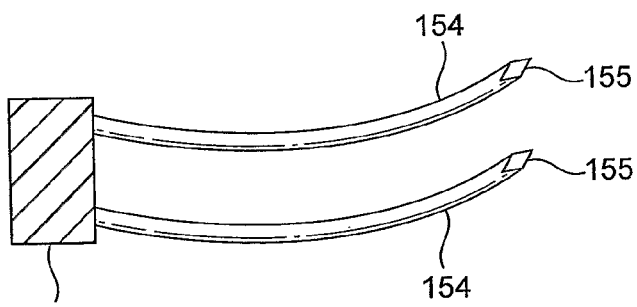
FIG. 26
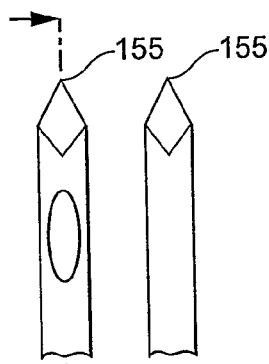
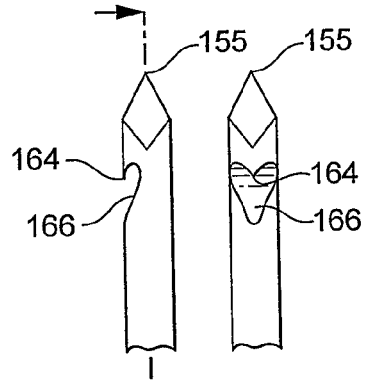
FIG. 27A　　　　　　FIG. 27B

TENDON REPAIR

This invention relates to an assembly for repairing torn tendons and in particular, although not exclusively, an assembly for the arthroscopic repair of a torn rotator cuff. The invention also relates to a method of repairing a torn rotator cuff and a cartridge and a needle assembly for the use with the assembly and method.

The rotator cuff, a group of four muscles that wrap around the shoulder joint to attach the upper arm to the shoulder blade, in part allows the shoulder to move and turn through a wider range than any other joint in the body, therefore allowing us to position our hands in order to perform day-to-day tasks. Unfortunately, tears of the rotator cuff are common, making many routine activities difficult and painful; prompt diagnosis and treatment can make profound improvements in these symptoms. Such injuries are caused by a number of mechanisms: repetitive mechanical wear against the bony arch of the shoulder blade can form defects in the tendons such as tears, or traumatic injury, such as falling on an outstretched arm, can pull the cuff off its bony attachment. The healing of such injuries can be complicated by a reduced blood supply to the tear.

Rotator cuff injuries are common, accounting for about ⅓ of presentations at shoulder clinics throughout the developed world, seen predominantly in the old, but also in the young. Younger patients often have had an accident leading to a traumatic injury, or used their shoulders excessively, as seen in professional athletes. As people age, the rotator cuff tissue loses some elasticity, becomes more susceptible to injuries, and is often damaged whilst performing everyday activities. However caused, if untreated or treated unsuccessfully, a long standing rotator cuff tear may lead to degeneration of the shoulder joint, possibly requiring a joint replacement.

Rotator cuff tears are treated through physical rehabilitation with limited success, and as such, surgery is necessary to correct the function of the muscle group. Rotator cuff repair surgery can be done either through a traditional large 6-10 cm incision, through a mini 3-5 cm incision, or using three to four small 1 cm incisions (referred to as 'portals') and a keyhole camera and instruments, called 'arthroscopy'. Large surgical incisions cause significant pain, often a persistent problem even after the rotator cuff tear has healed. Therefore, reducing the size of the wound used to repair the tear reduces pain after the operation, disrupts the joint less, allows for a quicker recovery time and therefore reduces the cost of managing such a condition.

Although the goal to re-attach the torn rotator cuff muscle is the same using all 3 methods, decreasing the size of the incision used increases the level of surgical skill required. As a result, the quality of repair produced arthroscopically using known methods may not have the same strength and integrity as an open rotator cuff repair.

In order to make the arthroscopic procedure easier, anchorage systems have been developed that require suture knots to be performed on the top side of the tendon. However, these suture knots are themselves prone to wear against the bone above the tendon (referred to as 'impingement'), either disrupting the repair, or further irritating and injuring the rotator cuff.

Traditional arthroscopic rotator cuff repair (ARCR) is a technically difficult procedure that leads to increased operative time and higher failure rates than its open equivalent for the same level of operative skill. In addition, the instruments used are more costly and often the procedure is labour intensive (primary and assisting surgeons are required). However, the advantages to ARCR often marginalize these potential problems; reduced peri-operative morbidity and associated length of hospitalization results in greater patient acceptance. Indeed, there is potential for the procedure to be conducted on an outpatient basis. Paramount to the success of ARCR is a systematic, step-wise approach to both operative planning and conduct by an experienced surgical arthroscopist.

U.S. Pat. No. 6,206,886 and U.S. Pat. No. 6,013,083 (Arthroscopic rotator cuff repair apparatus and method) describe the use of a cannula and drill guide plus a separate exterior tissue grasper to reduce or bring back the tendon onto its insertion site. This precludes its use as a purely arthroscopic technique. U.S. Pat. No. 6,206,886 also requires separate tissue grasping and fixation tools, calling for at least two separate arthroscopic portals being used at the same time and adding complexity to the surgical procedure.

U.S. Pat. No. 6,491,714 describes an apparatus for anchoring and reattachment of the rotator cuff but the solution involves a separate tissue grasper and a suture anchor that provides no reduction. U.S. Pat. No. 5,681,333 (Method and apparatus for arthroscopic rotator cuff repair utilizing bone tunnels for suture attachment) describes an arthroscopic device which requires a separate 'traction suture' to be used to hold the rotator cuff in its reduced position while conducting the fixation.

In U.S. Pat. No. 5,575,801 (Method and apparatus for arthroscopic rotator cuff repair), a device is presented that allows the tendon to be reduced during fixation, but this solution does not allow fixation through the strong lateral cortical bone of the humerus.

US 2004/0193217 and WO 2003/034895 give methods for arthroscopic tendon or ligament repair involving the use of a combination of tendon and/or bone anchors. Also known in the art are tissue clamps for use in arthroscopic surgery, (for example US 2005/0085850) and suture anchors for the attachment of connective tissue to bone (for example WO 2002/065892).

By pushing the tendon on to its insertion site (rather than pulling it, as in the prior art), the number of instruments or sequential steps required for repair is reduced, since gap reduction occurs on the same side of the joint as fixation. Advantageously, in rotator cuff repair, by combining arthroscopic fixation (by pushing the tendon onto the bone) of the rotator cuff with simultaneous reduction of the torn tendon onto its insertion site, arthroscopic repair of a rotator cuff is facilitated. The repair may be secured onto the strong cortical bone lateral to the tendon, thus minimising the possibility of impingement of the repair fixation material and providing a strong fixation. An even stronger repair may be achieved by the use of multiple sutures.

In one embodiment all manipulations are carried out medially of the shoulder such that, advantageously, the repair may be carried out through a single arthroscopic portal, for example a superior portal such as a Neviaser portal.

In other embodiments, gap reduction and fixation of the tendon is carried out medially of the shoulder while the repair is secured from the lateral aspect of the shoulder, advantageously allowing greater flexibility in configuring the repair assembly. Advantageously, the assembly may be operated entirely from the lateral side of the shoulder, thereby avoiding having to operate within the restricted space between a patient's shoulder and head. In one specific embodiment, the repair is sutured through the greater tuberosity of the humerus on an arcuate trajectory, thereby increasing the mass of bone retaining the sutures. This embodiment further allows an advantageous angle of approach of the repair assembly onto the tendon and the opposed lateral cortex of the humerus and better access through the relevant arthroscopic portals by defining an arcuate trajectory for the moving parts of the repair assembly.

Embodiments of the invention are now described by way of example only with reference to the accompanying figures in which.

Figure 1:
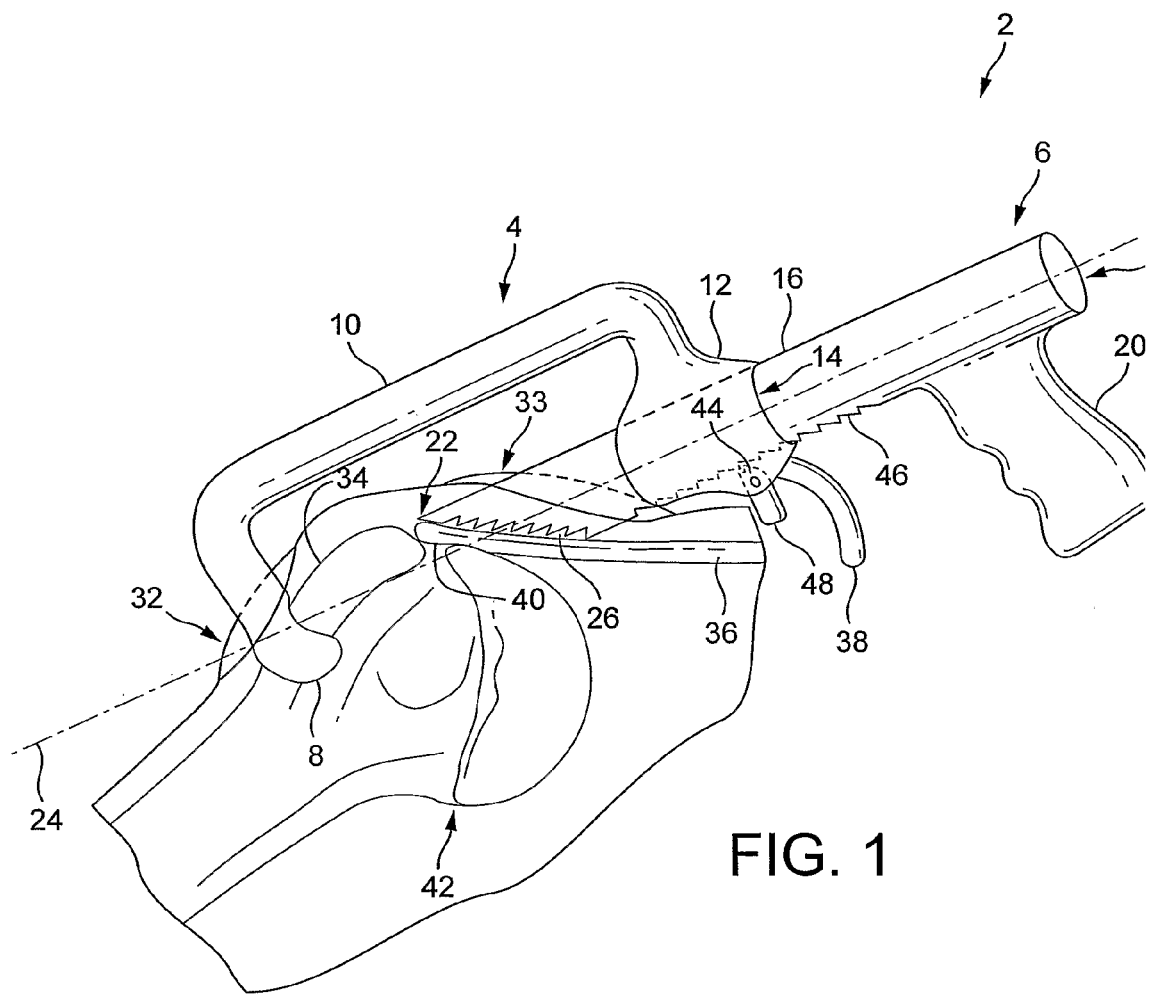
FIG. 1 shows one embodiment of a rotator cuff repair assembly engaged with a rotator cuff tendon and the humeral head.
Figure 2:
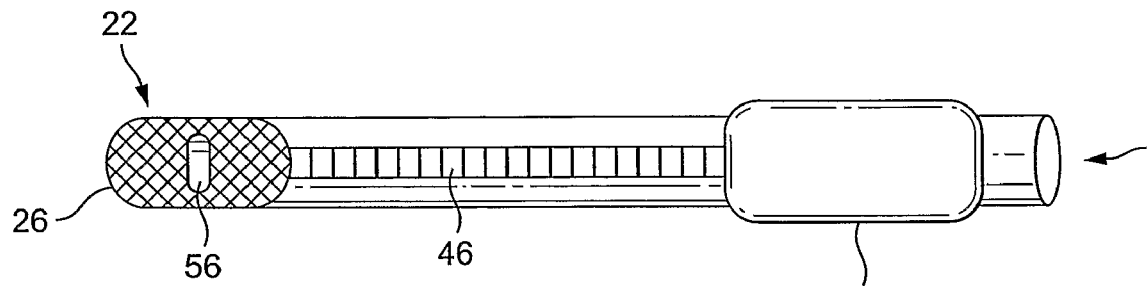
FIG. 2 shows a gap reducing portion of the assembly shown in FIG. 1.
Figure 14:
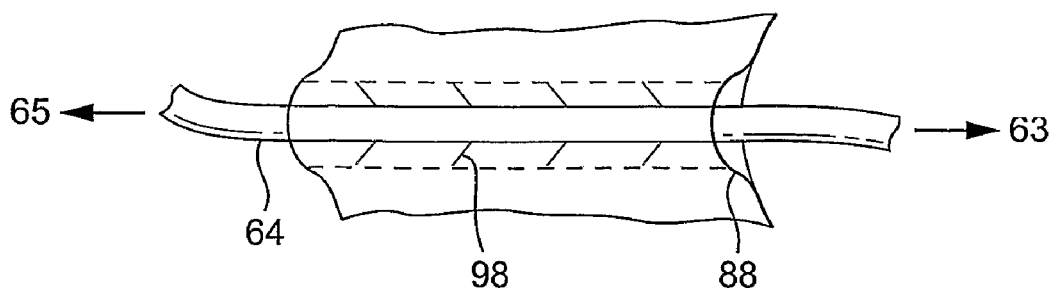
Figure 12:
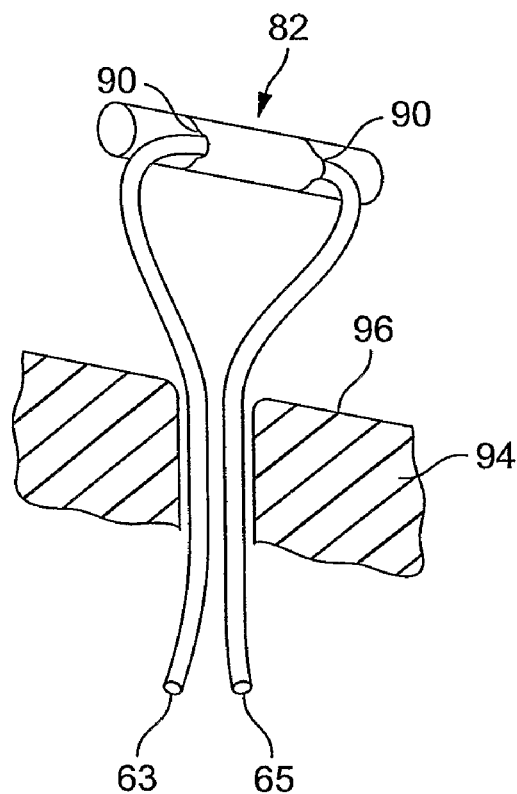
Figure 13:
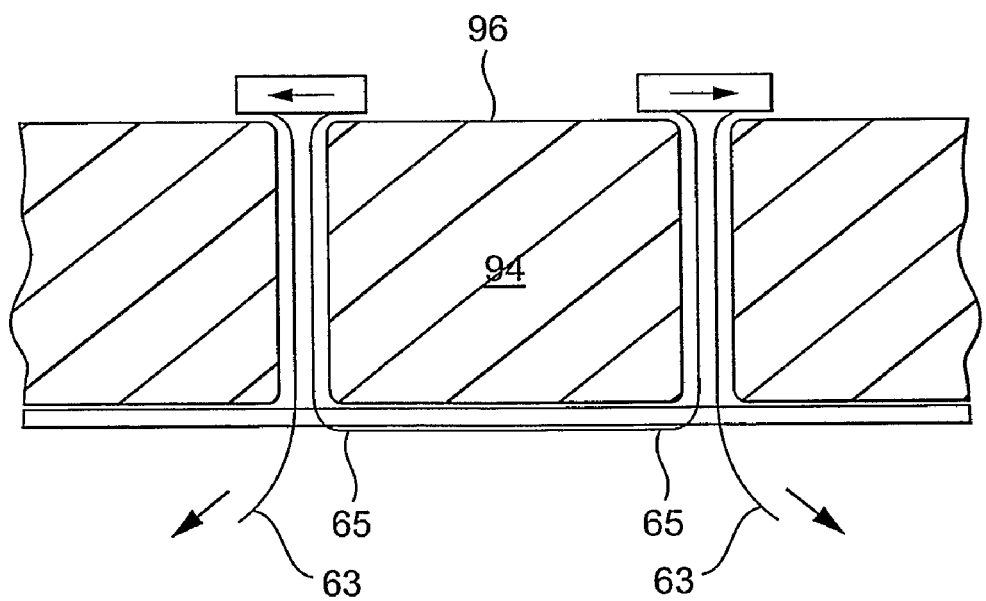
Figure 15:
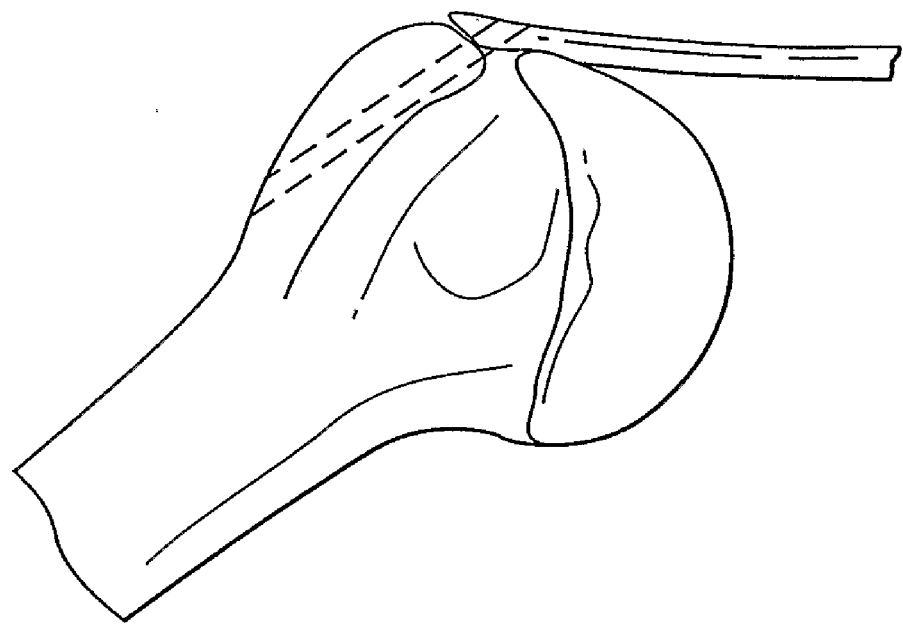
Figure 16:
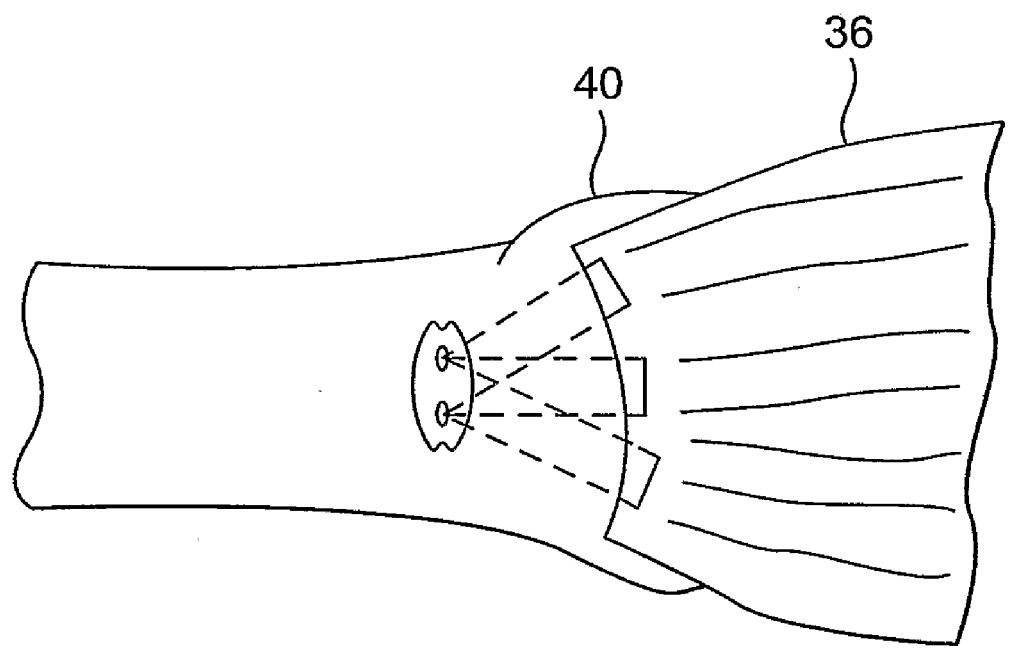
Figure 17:
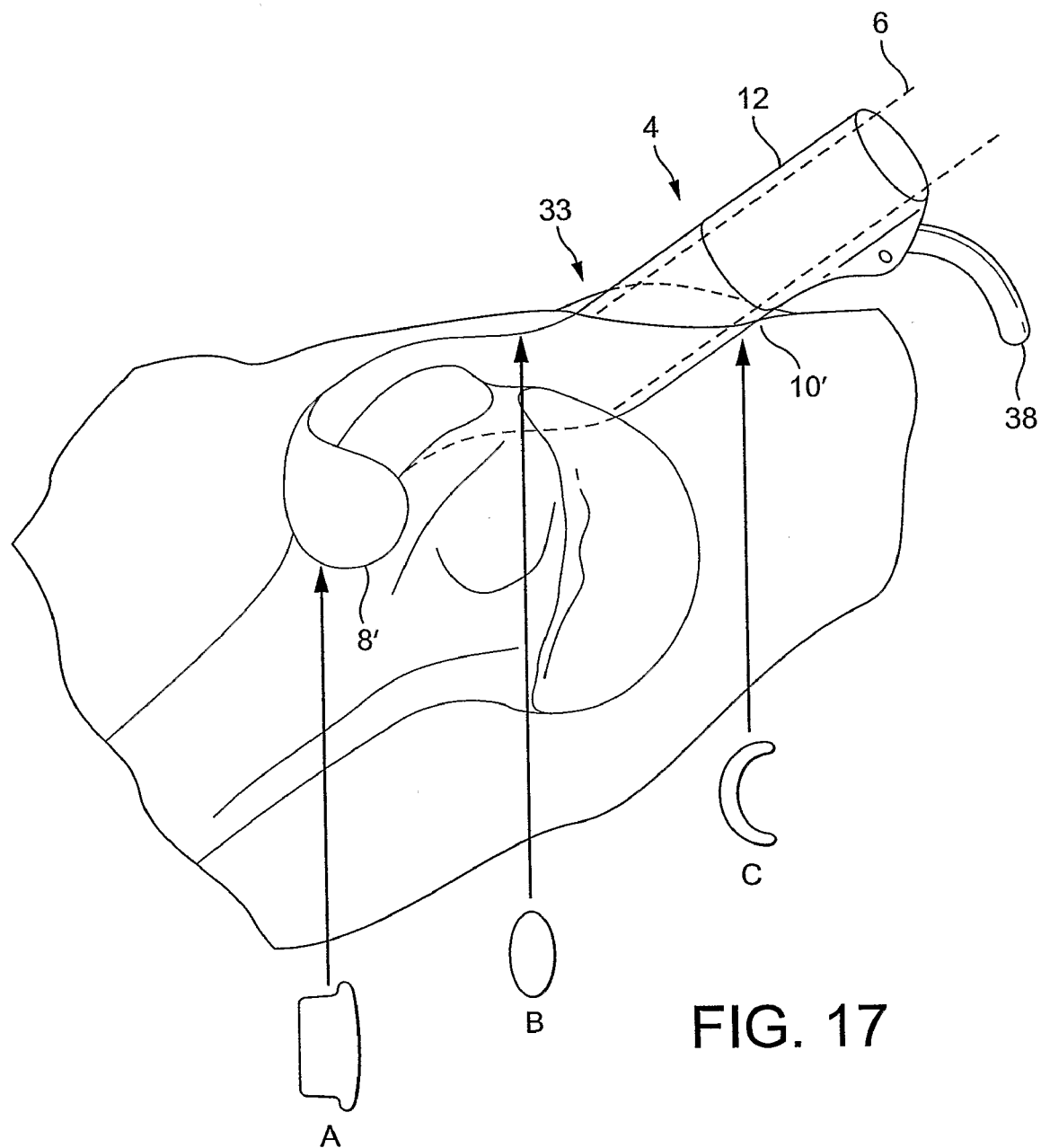
Figure 18A:
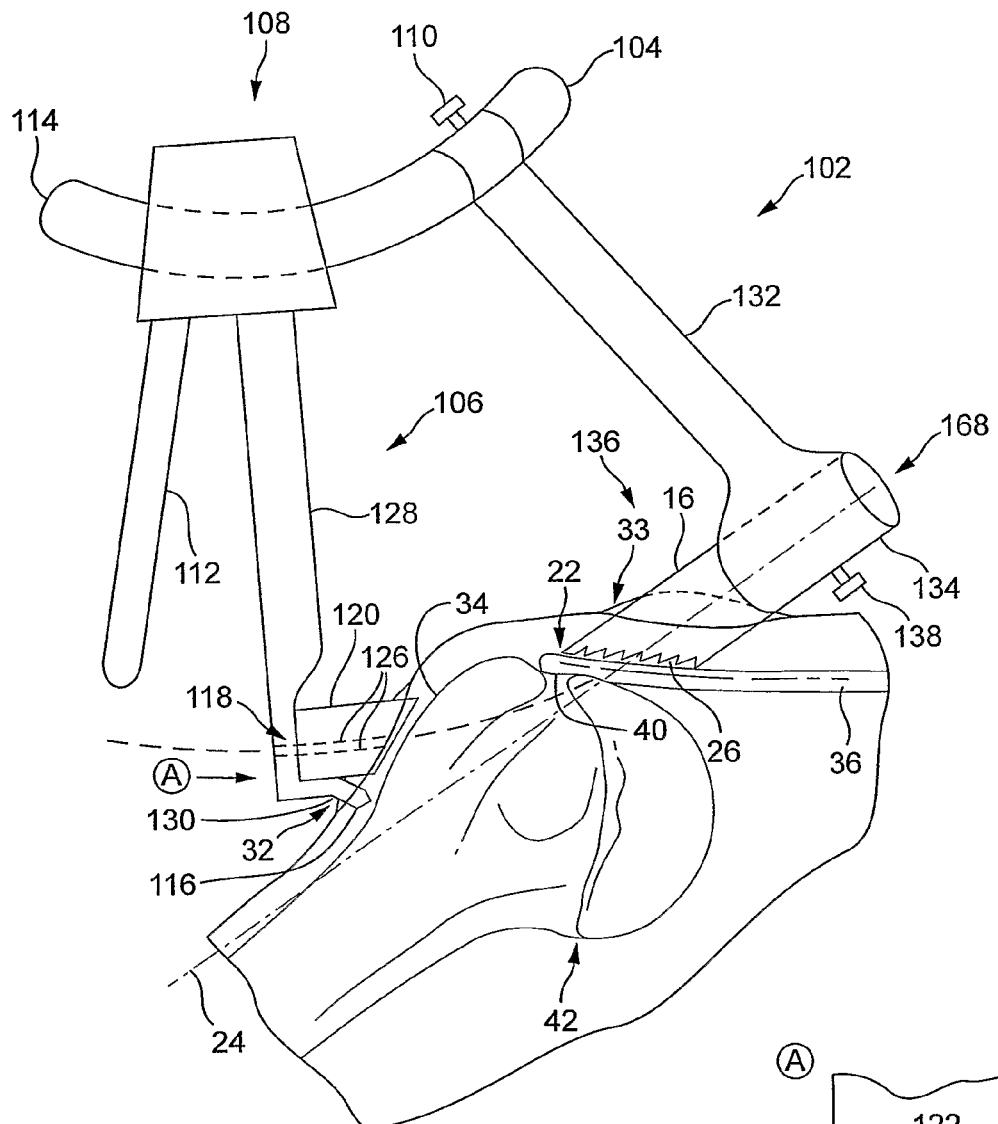
Figure 19:
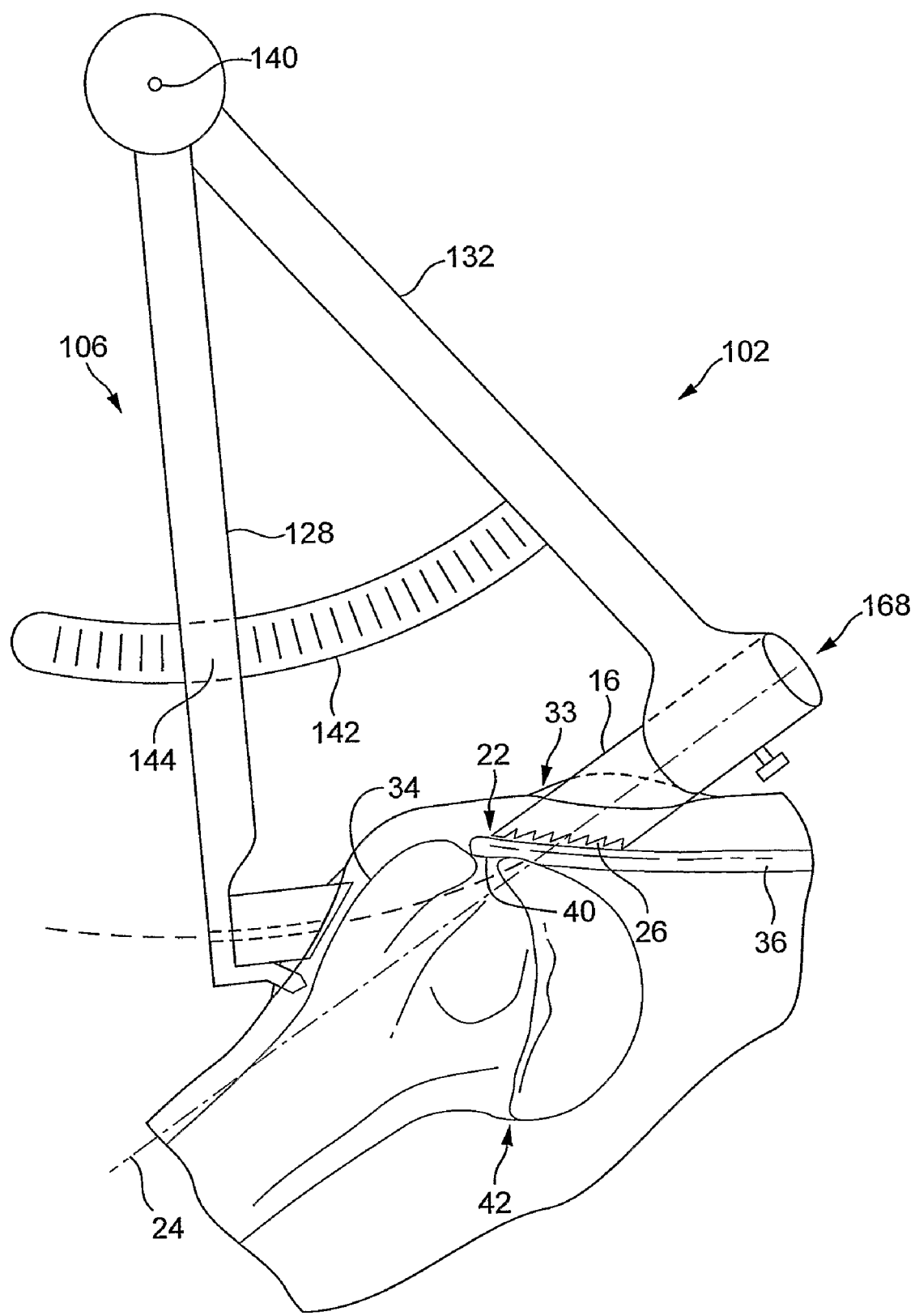
Figure 20:
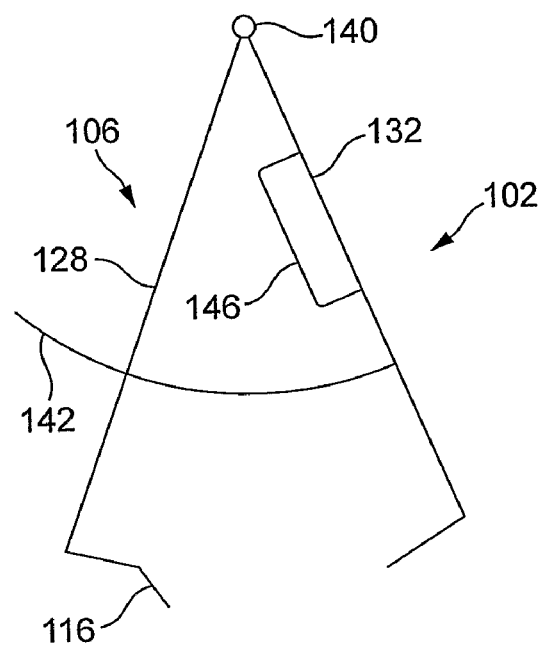
Figure 21:
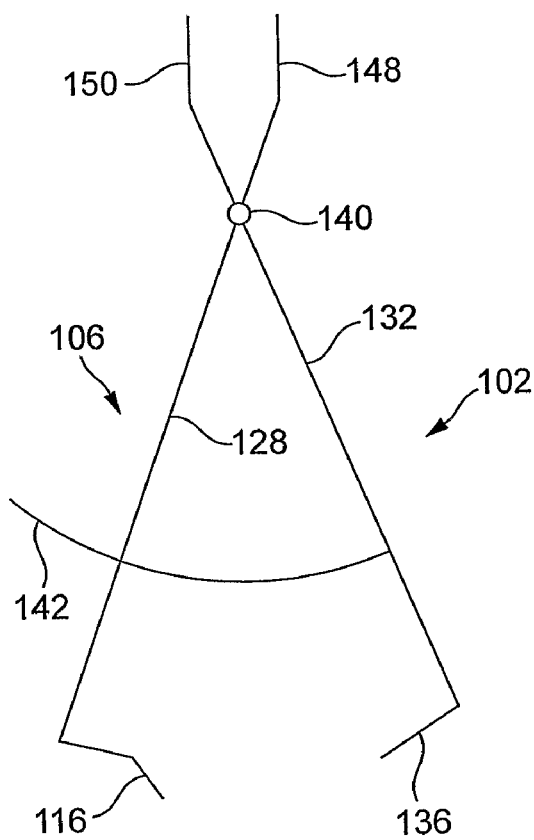
Figure 22A:
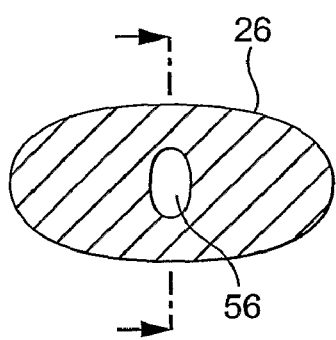
Figure 23A:
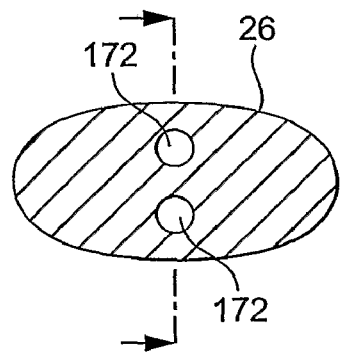
Figure 23B:
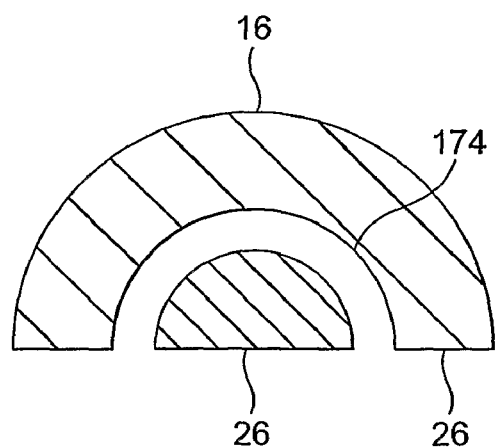

FIGS. 12 and 13 schematically show the deployment of a suture toggle;

FIG. 14 shows a channel for securing a suture to the toggle;

FIGS. 15 and 16 schematically show a completed repair;

FIG. 17 shows an alternative guide hook for the assembly of FIG. 1;

FIGS. 18A and B show an alternative embodiment of the rotator cuff repair assembly;

FIG. 19 shows a further, related embodiment of the rotator cuff repair assembly;

FIGS. 20 and 21 depict arrangements for actuating the FIG. 19 embodiment;

FIGS. 22A, B and C and FIGS. 23A and B depict various embodiments of a tendon engaging member and cross-sections there through;

FIGS. 24A and B show alternative embodiments for a force distribution or pressure reduction device for a suture;

FIGS. 25A and B show a one-way suture mat;

FIG. 26 show a bone piercing tool; and

FIGS. 27A and B show enlarged views of various tip arrangements for the bone piercing tool of FIG. 26.

Although the present embodiments of a device for rotator cuff repair can be used in either a 'beach chair' (sitting) or a 'lateral decubitus' (side-lying) position under general anaesthesia, the former position enables optimal positioning of the device, and manipulation of the operative arm during the procedure, both of which aid the success of the procedure. Although the shoulder is manipulated throughout the procedure, the control position whilst seated in the 'beach chair' position is with the elbow by the side and the forearm rested across the patient's torso.

Small (5-10 mm) portal incisions are created in the back (posterior portal), side (lateral portal), front (anterior portal) and top (superior portal, for example a Neviaser portal) of the shoulder in order to allow visualisation and instrumentation of the joint and cuff tear. As is optimum practice, a complete diagnostic arthroscopy (inspection of the shoulder joint) and bursoscopy (inspection of bursa) is initially performed. Care is taken to inspect the biceps tendon within the shoulder, the cartilage surfaces of the head and glenoid, the passive stabilising anatomy and the rotator cuff tendons, addressing any pathology after complete inspection.

Once visualised, the joint and cuff must be prepared for repair. Pre-operative evaluation of the acromion and intra-operative evaluation serves as a guide to the extent of acromioplasty necessary; the goal is to smooth and flatten the under-surface of the acromion to provide more room for the repair and to relieve pressure from the healing tendon, as is common practice in rotator cuff repair in the UK.

The rotator cuff tear is then visualized through the most appropriate portal. The size and pattern of the tear is assessed. Any thin or fragmented portions are removed and the area where the tendon will be reattached to the bone is vigorously (or possibly only lightly) debrided to encourage new blood vessel ingrowth for healing. This debridement is arthroscopic using a burr or drill and can be effected to remove all cartilaginous and cortical bone at the native rotator cuff humeral insertion.

The repair procedure using embodiments of the present device is described in detail further below in conjunction with a detailed description of the structure of the device. In brief, the tendon is reduced onto its insertion site by exerting a pushing force and a suture is driven through the tendon and the humeral head, either both from a superior portal, or the suture may be retrieved medially to laterally from a lateral portal.

At the completion of the procedure, the shoulder is injected with a long acting local anesthetic to assist with postoperative pain management. Each portal incision is closed with one or more skin stitches (depending on incision size) and covered with 'steri-strip' tapes, followed by a dry sterile dressing. A compression dressing is also used to reduce post-operative bleeding and mobility. This further assists in pain and swelling management. Finally, a shoulder sling or brace is applied for immobilization and site protection. The position of immobilisation may be 30 degrees of abduction and neutral rotation, for example using a 30 degree abduction wedge.

Post-operative care is not device specific, but is dependent upon the facilities available and local management guidelines. Commonly, patients are instructed in a gentle (recovery phase I) range of motion 1-2 days post-operatively, beginning with gentle passive flexion-extension pendulum movements in external axial rotation. After post-operative day 2, the compression dressing can be removed and the use of the operative sided hand can be encouraged, whilst maintaining the elbow at the side, although active motion with elbow away from the side should be discouraged. 4-8 weeks post-operatively, the patient can progress to pain free active movement (recovery phase II), although resistive exercises should be reserved for 10-12 weeks post-surgery.

With reference to FIG. 1, one embodiment of the repair device includes an assembly whose principle components are a hook guide 4 and a gap reducing portion 6 which is guided by the hook guide 4.

Figure 3:
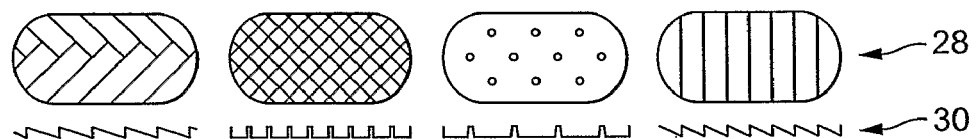
FIG. 3 shows a number of profiles for a tendon engaging surface of the gap reducing portion of FIG. 2.
Figure 4:
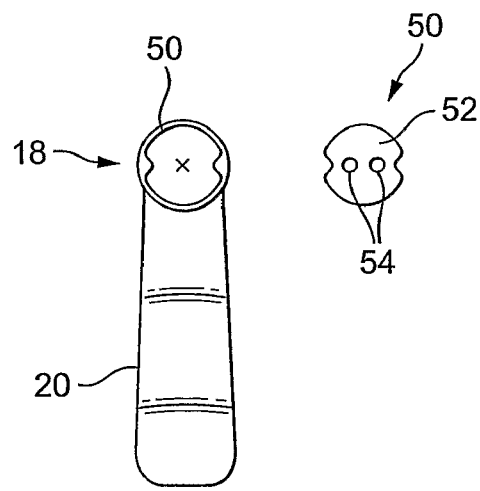
FIG. 4 shows an end view of the gap reducing portion of FIG. 2 and a frontal view of a cartridge for insertion into the gap reducing portion.

The hook guide 4 includes a bone engaging hook 8 and connected thereto by an angled neck portion 10 a guide portion 12. The guide portion 12 defines a cylindrical guide channel 14 which is arranged to accept a cylindrical elongate portion 16 of the gap reducing portion 6. At a first end 18 of the gap reducing portion 6 extends a handle 20. At a second end 22 of the gap reducing portion, the end surface of the gap reducing portion 6 is angled with respect to a longitudinal axis 24 of the gap reducing portion 6 to form a tendon engaging surface 26. The tendon engaging surface 26 may be barbed or patterned in a number of ways as indicated in FIG. 3 (plan view 28 and cross-sectional view 30) in order to provide a secure grip on the tendon.

In use the hook guide portion is inserted through a lateral portal 32 and the hook is hooked around the greater tuberosity 34 on the lateral aspect of the shoulder. The hook is designed to fit around the posterolateral curve of the humeral head and the neck portion 10 is angled such as to protrude out of the lateral portal and extend in a medial direction so that the guide 12 is positioned such that it can guide the gap reducing portion through the superior portal. With the hook in place, the gap reducing portion 16 is advanced longitudinally through the guide portions 12 to engage the torn tendon 36. The gap reducing portion is advanced by squeezing the handle 20 against a lever 38 protruding from the guide portion 12.

As the gap reducing portion is advanced and contacts the torn tendon 36, it exerts a force both pushing the tendon against the upper surface 40 of the humeral head 42 and at the same time exerts a force on the tendon sliding it along the upper surface in a lateral direction such that gap between the torn rotator cuff tendon 36 and its bony insertion site is reduced. This dual effect of pushing the tendon against the humeral head and at the same time advancing it laterally in order to reduce the gap is due to the angled arrangement of the tendon engaging surface 26 such that the longitudinal axis 24 along which the gap reducing portion is advanced has a component both parallel and perpendicular to the upper surface 40 of the humeral head.

The guide 12 includes a pivotal pawl 44 which protrudes into the cylindrical channel 14 such that it engages a toothed surface 46 on one aspect of the gap reducing portion. The toothed surface 46 and the pawl 44 cooperatively define a ratchet mechanism such that the gap engaging portion can be freely advanced against the tendon and humeral head but is blocked from retracting. This way, the tendon 36 is easily held in place once it is tensioned to reduce the gap of the tear. The grip on the tendon can be released by pulling a pawl lever 48 in a direction towards the handle 20.

The longitudinal portion 16 is hollow and adapted to accept under guidance a cartridge 50 which has an outer surface complimentary to the inner surface of the longitudinal portion 16. The cartridge is adapted to be inserted into the gap reducing portion with its front face 52 towards the tendon engaging surface 26 such that a first and second aperture 54 in the front surface 52 is lined up with a corresponding longitudinal aperture 56 in the tendon engaging surface 26 so that a needle being advanced out of each aperture 54, as well as a loop of suture between the needles can pass through the longitudinal aperture 56, as described in more detail below.

Figure 5:
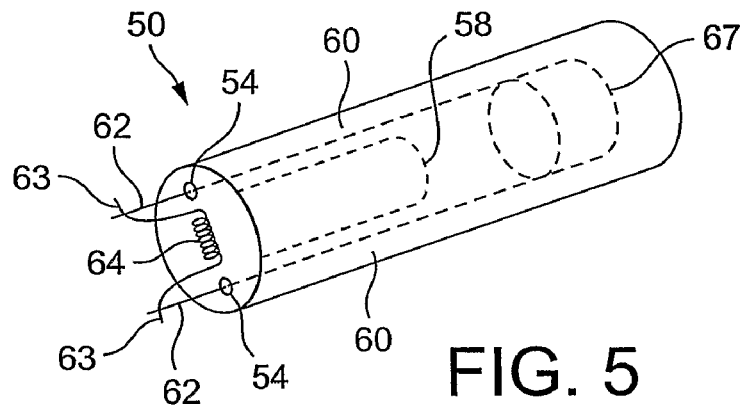
FIG. 5 shows a perspective view of the cartridge.
Figure 6:
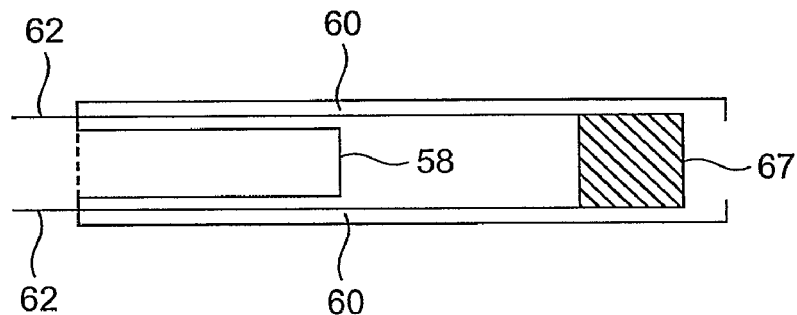
FIG. 6 shows a cross-sectional view of the cartridge.

FIG. 5 shows a schematic perspective view of the cartridge 50 and FIG. 6 shows a plan view. Extending inwards from the front end 52 of the cartridge is a guide element 58 defining a guide channel 60 between the cartridge and the guide element. A pair of needles or prongs 62 is disposed within the guide channels 60 such as to be deployable through apertures 54. The pair of needles 62 is joined by a cross member 64 inside the cartridge. It is understood that at least part of the cartridge may alternatively be implemented as part of the gap reducing portion.

The cross member 64 is engaged by a drive mechanism (not shown) provided on either the cartridge or the gap reduction portion and which is arranged to drive the needles 62 through the apertures 54 and 56 in a direction towards the hook 8. The drive mechanism may, for example, be implemented as a threaded screw or a manual or geared squeeze mechanism, which would allow fine control of the depths of the deployment of the needles 62 or a spring loaded mechanism which could be used to "fire" the needles through the tendon and bone. Alternatively, the cross member 64 may be arranged to define a contact surface for a hammer or mallet such that the needles can be driven forward as indicated above by tapping on the contact surface.

As shown in FIG. 5, the two needles are loaded with a single length of suture 64, with one end 63 of the suture 64 being passed through an eye of each corresponding needle 62. The suture is arranged such that a relatively short end of the suture protrudes from each end of the needles with the remaining suture material being coiled up or otherwise stored between the two needles 62.

Figure 7:
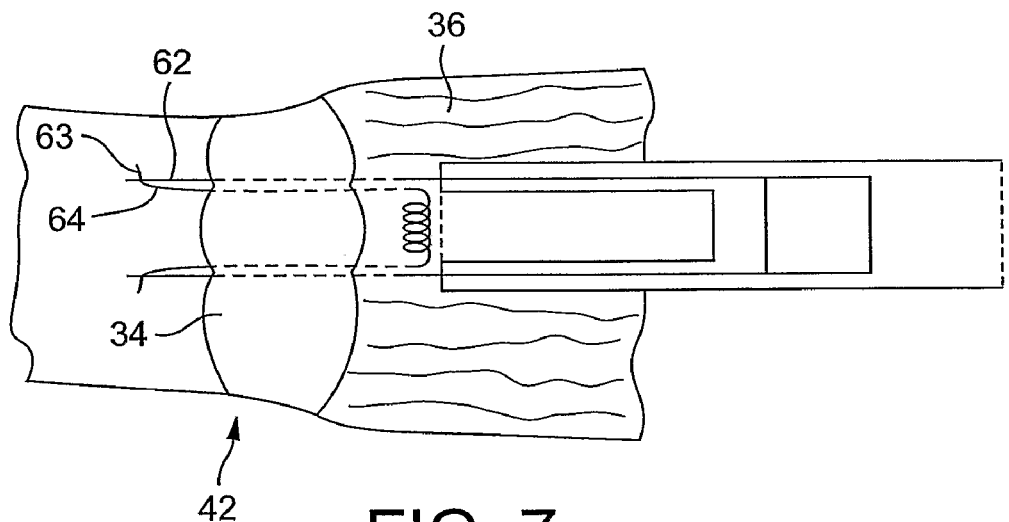
FIG. 7 shows a schematic view of the cartridge being deployed in rotator cuff tendon repair.

In use, as illustrated in FIG. 7, the needles 62 and suture 64 are driven through the rotator cuff tendon and the humeral head 42 such as to create an oblique medial to lateral suture passage through the greater tuberosity 34 and to emerge on a lateral side of the humeral head.

A number of options are envisaged for capturing and securing the suture as it emerges on the lateral side of the humeral head.

In one embodiment, the hook 8 defines a holder for holding a suture mat such that the suture mat is held against the lateral aspect of the greater tuberosity in a location where it is intersected by the longitudinal axis 24. The holder is arranged such that it holds the suture mat in place sufficiently secure such that it is in contact with the lateral aspect of the tuberosity when the device is in place for repair but can be released with sufficient ease once the device is removed following capture of the suture 64 by the suture mat, as described below.

The needle and suture are driven through the bone until they emerge on the lateral side, puncture the suture mat and the free ends 63 of the suture have traversed the suture mat. The suture is thereby captured by the suture mat which is made from materials suitable for this purpose, and the suture is thus secured by the suture mat. The suture cartridge 50 can be retracted from the bore of the longitudinal portion 16 by a retrieval tie attached to the cross member 64 surface, or a spring loaded mechanism (not shown) which could be used to "eject" the cartridge 50 out of the bore of the longitudinal portion 16, and additional cartridges 50 accepted into the longitudinal portion 16 under guidance.

Once the suture is secured by the suture mat, the arm may be manipulated to reduce the tension on the suture material by adapting the glenohumeral joint to more than 90° in the scapula plane. Mid abduction, the gap reduction portion can be released by activating the lever 48 to pivot the pawl 44, thereby releasing the ratchet mechanism maintaining the gap reducing portion in place. The hook guide can then be removed from the operative site.

Once the unloaded position is optimised, the suture can be tied (sliding/locking knot placed on primary suture post, slide knot to cortical bone, use pressure to secure and lock with pull of opposite suture post, before switching post and completing with multiple half stitches in a manner known to the skilled person) from the lateral portal. Alternatively the suture may be tied between the hook and bone with the hook in place and the device engaged from a further lateral portal.

Figure 8:
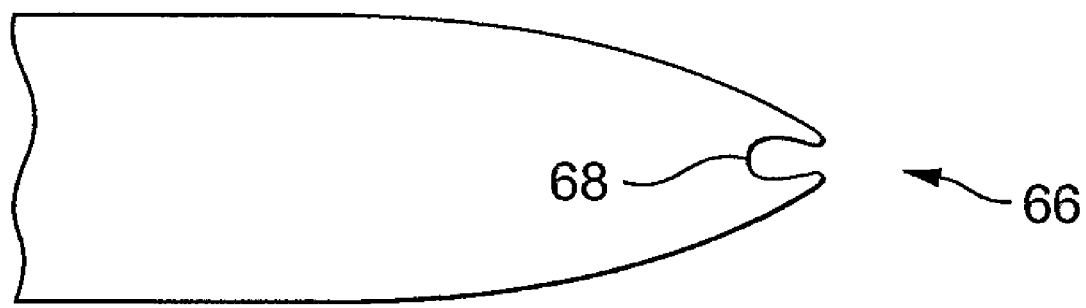
FIGS. 8, 9 and 10 show several configurations of a needle of the cartridge.
Figure 9:
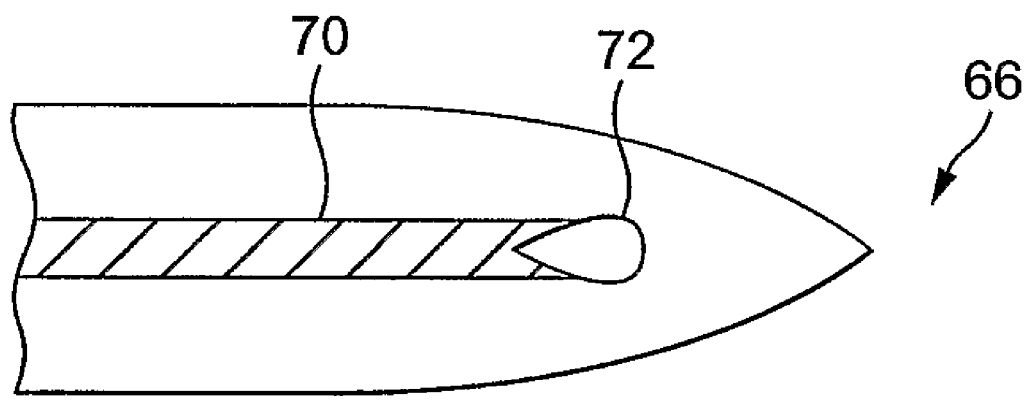

The tip 66 of the needles 64 may have a modified eye for accepting the suture 64. The modified eye 68 depicted in FIG. 8 is open towards the tip 66 such that the suture can simply slide off the tip 66 as the needle is withdrawn. As shown in FIG. 9, the needle may define a recessed longitudinal channel 70 which extends away from a conventional needle eye 72 and the tip 66. As the needle runs through the bone as it is being advanced, the suture lying in the recessed channel 70 experiences less friction than otherwise. The same applies as the needle is retracted. Evidently, the channel 70 of the FIG. 9 embodiment can be combined with the modified open needle eye 68 of FIG. 8.

The capture of the suture by the suture mat may be facilitated by an arrangement whereby the needles of the FIG. 9 embodiment are mounted rotatably and the suture is guided and tensioned by a suture guide in the cartridge. By rotating the needles (for example by a ¼ turn, or 90°) once the suture is captured in the suture mat, the tension in the suture acts to urge it out of the channel 70, thereby facilitating capture by the suture mat The pull-out of the suture from the needle may further be prevented by a stopper or a knot.

In an alternative embodiment, the suture is provided with a toggle which is pushed through the bone channel created by the needle and, by engaging the lateral aspect of the humeral head, prevents the suture from slipping back. This embodiment may be used together with the suture mat described above or without it since the suture is now captured by the toggle. The toggle can be used in two different ways. First, analogously to the embodiment described above whereas the toggle is used only for preventing pull-back and the suture is tied on the lateral aspect of the humeral head described above. Second, the toggle may be left permanently in place and the sutures tied on top of the humeral head from the superior portal as described in more detail below. In the first approach, a relatively short length of suture is provided at the free end 63 of the suture 64 such that it exits from the lateral aspect of the humeral head and can be retrieved from the lateral portal. In the second approach, a much longer length of suture is provided at the free end 63 such that the free end 63 remains accessible on top of the tendon from the superior portal, as described in detail below with reference to FIGS. 10 to 12.

One possible needle for use with the toggle embodiment described above is depicted in FIG. 10 and comprises a relatively thicker tip portion 74 and a relatively thinner (with respect to the portion 74) stem portion 76. The needle eye may be provided close to the junction between the stem portion 76. The open needle eye of the FIG. 8 embodiment may be used in conjunction with thicker tip portion 74, as shown schematically by alternative needle eye 80 (dashed lines) in FIG. 10. It is understood that the FIG. 10 needle configuration may be combined with any of the configurations described above.

Figure 10:
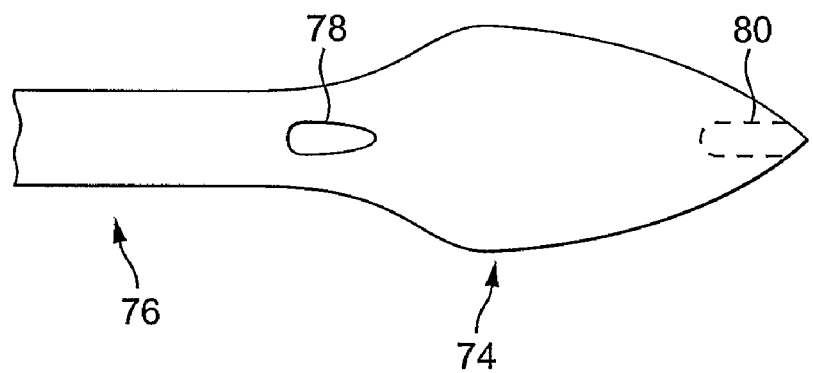
Figure 11:
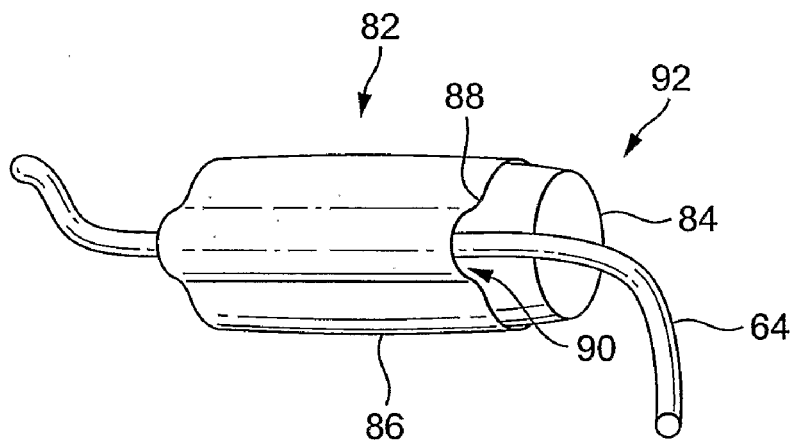
FIG. 11 shows a suture toggle for ensuring engagement of the suture on the lateral aspect of the humeral head.

A toggle 82 for use with the needle of FIG. 10 is shown schematically in FIG. 11 and comprises a resilient, hollow cylindrical member 84, adapted to loosely fit around the stem portion 76 such that its outer diameter is less than or equal to the diameter of the thicker tip portion 74. The cylindrical portion 84 is arranged to be sufficiently elastic such that it can be pushed across the tip portion 74. The cylindrical portion 84 includes a sleeve 86 with the suture 64 disposed in a channel 88 defined by the sleeve 86.

In use, the needles of the cartridge are provided with a toggle 82 around the stem portion 76 with the free end 63 of the suture threaded through eye 78 or 80. Once the needle has been pushed through the bone of the humeral head such that the tip 74 emerges completely on the lateral aspect thereof, the toggle 82 is advanced along the stem 76 through the bone channel created by the tip 74 and is pushed out on the lateral side of the humeral head across tip 74. The toggle may be advanced by any suitable means, for example by a further sleeve provided around stem 76 of the needle which can be advanced by a plunger type mechanism.

In the first method described above, once the toggles of both needles have been deployed on the lateral side of the humeral head, the needles are retracted and the hook guide and gap reducing portion are removed, ensuring an appropriate position of the arm as described above. The free end 63 of the suture and the toggle 82 can then be accessed from the lateral portal, the toggles removed and the suture tied as described above in conjunction with the suture mat.

In the second method described above, the free end 63 is sufficiently long such that it remains on top of the tendon accessible from the superior portal. As shown in FIG. 12 once the repair device has been removed, the site is left with a toggle 82 protruding from a channel left by each needles with a loop of suture connecting the two respective toggles on top of the tendon and the free end 63 being accessible from the superior portal.

The sleeve 88 of the toggle 82 covers only a portion of the toggle so that the point of attachment 90 of the suture 64 to the toggle 82 is on the main body of the toggle leaving at least one free end 92 of the toggle such that once the suture is tightened by pulling on the free end 63 the toggle is rotated into a transverse position with respect to the channel left by the needle in the bone 94 such that it engages the lateral surface 96 of the bone. The free ends 63 from each channel can then be tied on top of the tendon in any suitable fashion, although preferably the point of attachment 90 of the suture 64 to the toggle 82 provides enough tension to not require further fixation by tying the free ends 63 of the suture 64.

As shown in FIG. 14, the channel 88 may be provided with barbs 98 or any other suitable one-way means such that the suture can be moved with respect to the toggle by pulling on the free end 63 only in the direction indicated by the arrows in FIG. 13. This arrangement allows the suture to be secured without the need for tying it on top of the tendon although, of course, the free ends 63 may be tied on top of the tendon in order to additionally secure the repair.

It is understood that the toggle system described above will also find application in other repair devices, for example using only a single needle, and that in a further aspect of the invention there is provided a surgical needle which has an enlarged tip portion which is of a larger cross-section than a stem portion of the needle extending from the enlarged portion away from the tip. There further is provided a toggle including a sleeve of resilient material surrounding the stem portion and defining a longitudinal channel for accepting a suture for use with such a needle.

FIG. 15 shows a side view of the resulting repair. As depicted in the plan view of FIG. 16 the tendon 36 is preferably secured to the humeral head 40 by further sutures deployed as described above. For example, sutures may be placed medial to the tendon edge and one centimeter apart from each other, covering the front to back extent of the tendon.

In an alternative embodiment of the hook guide 4, which is arranged such that the hook guide and gap reducing portion 6 can both be deployed through the superior portal rather than through both the superior and lateral portal 32 as described with reference to FIG. 1. The guide portion 12 is attached to an alternative hook 8', which is adapted to fit over the humeral head, by a straight neck portion 10' which is hollow such as to accept the gap reducing portion therein. When the device is assembled the neck portion extends straight from the guide 12 along the gap reducing portion 6. In the vicinity of the point of contact between the gap reducing portion and the tendon, the neck portion 10' curves around the humeral head. The insets A, B and C in FIG. 17 indicate the corresponding cross-sections of the neck 10'.

Figure 18B:
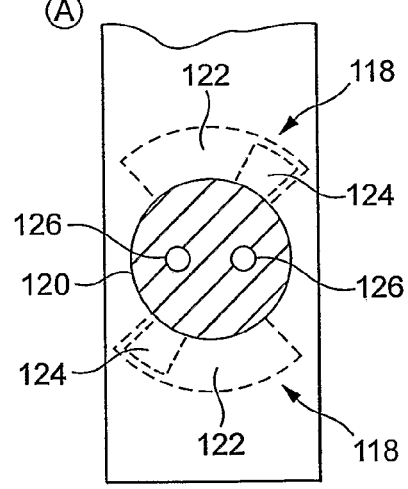

In alternative embodiments of the tendon repair assembly now described with reference to FIGS. 18 and 19, the tendon repair assembly generally includes a gap reducing portion 102 and a bone engaging portion 106 as for the embodiment described above. The gap reducing portion 102 is linked to the bone reducing portion 106 by a guide member 104, for example an arcuate guide rod, and a drive mechanism 108 riding on the guide member 104 and being attached to the bone engaging member 106. The gap reducing member 102 may be secured to the guide member 104 by a grub screw 110 or alternative releasable securing means but it will be understood that gap reducing portion 102 may instead be fixedly secured to the guide member 104. Equally, the bone engaging portion may be secured to the drive mechanism 108 either fixedly or removeably.

The drive mechanism 108 may be any suitable drive mechanism for advancing along the guide member 104 to move the gap reducing portion 102 and the bone engaging portion 106 relative to each other, for example the drive member 108 may be linked by a threaded rotational drive mechanism. In one particular example, the drive mechanism 108 includes a catch and release plate mechanism as commonly found in a typical caulking gun or similar dispenser arrangements. In such arrangements, a piston is advanced into a caulk cartridge by means of a trigger-actuated catch plate which bites on a drive rod to advance it when the trigger is pressed and retreat of the piston is blocked by a releasable brake plate biting on the drive rod which can be released to allow retracting the piston. The drive mechanism 108 may include a similar arrangement in which a catch plate mechanism is activated by a trigger 112 to drive the bone engaging member 106 towards the gap reducing member 102 along the guide member 104. Accordingly, such an arrangement will differ from a caulking gun drive mechanism mentioned above in that the trigger 112 is activated by the palm of a user against the bone engaging portion 106 held by the user's fingers (whereas in a typical caulking gun the trigger will be activated by the user's fingers against a butt resting on the user's palm). Consequently, it is the free end 114 of the guide member 104 which corresponds to the free end of a piston in a caulking gun.

Bone engaging portion 106 comprises at the lower end thereof a bone engaging member 116, for example including one or more spikes to securely engage with the humeral cortical bone through the lateral portal 32. If the bone engaging member 116 consist of a single spike, the repair assembly may advantageously be rotated around this single spike to allow greater flexibility in the placement of the device, for example to avoid obstacles such the patient's head. On the other hand, a more fixed arrangement can be achieved by using two or more spikes which hold the assembly in a substantially fixed relationship with respect to the bone.

The bone engaging portion 106 defines a connector arrangement 118 adjacent the bone engaging member 116, for a guide member 120 which can be removeably connected to the bone engaging portion 106. For example, the connector arrangement 118 may comprise a bayonet coupling including bayonet slots 122 defined in the bone engaging portion to engage with bayonet lugs 124 defined on the guide member 120. It will be understood that any other suitable connector arrangement could be used in place of a bayonet coupling, for example a threaded connection or click fit connection. When connected, the guide member 120 is arranged to be deployed together with the bone engaging member 116 through the lateral portal 32 but may be removed to allow increased access to the lateral side of the humerus through the lateral portal or exchanged for an alternative guide member as described in more detail below. The guide member 120 defines two channels 126 for guiding a bone piercing tool, again as described in more detail below.

The bone engaging portion 106 comprises a linking member 128 to which the bone engaging portion is connected by a spacing member 130 adjacent to connecting arrangement 118. The length of the spacing member 130 can be selected to trade off accessibility of the lateral side of the humerus through the lateral portal and overall compactness of the repair assembly wherein a larger length results in greater accessibility but also increased dimensions of the device. The surface of the spacing member 130 may be shaped such as to co-operate with the guide member 118 to provide additional support to the guide member.

Turning now to the gap reducing portion 102, this comprises a linking member 132 connected at one end to the guide element 104 and defining a connector 134 at an opposed end. The connector 134 is arranged to connect a tendon engaging member 136 to the link member 132 comprising a longitudinal member 16 which defines a tendon engaging portion 26 as in the previously described embodiment. The connector comprises, for example, a sleeve accepting the tendon engaging member 136 secured by a grub screw 138 but it will be understood that many other connectors or mechanisms may be used, for example, a bayonet connector or click fit connector. Evidently, the tendon engaging member 136 may be permanently secured to the linking member 132 instead.

Advantageously, by releasably connecting the tendon engaging portion 136 to the linking member 132, the tendon engaging portion can be placed through the Superior portal in a convenient fashion like a conventional cannula and can then be connected to the remainder of the arrangement once in place. The transverse dimensions of the tendon engaging member on the one hand and the bone engaging member 116 and guide element 120 on the other hand should each not exceed appropriate dimensions for placing them through arthroscopic portals, for example 10 mm. Specifically, the elongate member 16 may have a typical diameter of 8 to 10 mm.

To provide sufficient clearance of the shoulder, the linking members 128 and 132 may have a length of about 10-15 cm, defining a corresponding radius of curvature of about 15-20 cm at the tendon engaging surface. It will be understood that the members may be configured to have an adjustable length, for example by a telescopic arrangement.

In an alternative embodiment, now described with reference to FIG. 19, the linking members 132 and 128 are elongated to intersect each other and are pivotably secured to each other by a pivot 140. A one-way retaining member 142 is secured to one of the linking members for example linking member 132 and engages a corresponding portion of the other linking member, for example linking member 128 to define a one-way clutch. For example, this may be implemented as a ratchet mechanism between a contact area 144 on link member 128 and the retaining member 142 but other one-way mechanisms are equally envisaged for example a smooth retaining member held in a one-way frictional clutch, for example an excentric cam arrangement. It is understood that the one-way mechanism may also be incorporated in or associated with the pivot 40.

In use, a user squeezes the gap reducing portion 102 against the bone engaging portion 106 such that the tendon engaging surface 26 pushes on to the tendon and reduces the gap medially to laterally as described above moving towards the bone engaging portion 106 about the pivot 140. To this end, the link members 132 and 128 may include shaped portions to facilitate being held in a user's palm and fingers to allow the two portions to be squeezed together. In a further alternative arrangement depicted in FIG. 20, a handle 146 for accepting a user's fingers may be provided on one of the portions for example the gap reducing portion 102 to facilitate squeezing the two portions together. In yet a further alternative, the two linked portions 132 and 128 are extended beyond the pivot 140 to end in respective grip portions 148 and 150 to result in a forceps like arrangement in which the tendon engaging member 136 is advanced against the bone engaging member 116 by squeezing together the grip portions 148 and 150.

As the drive mechanism 114 is activated or the link members 128 and 132 or grip portions 150 and 148 are squeezed together as described with reference to FIGS. 19 to 21, the tendon engaging surface 26 of the tendon engaging member 136 advances towards the bone engaging member 116 on an arcuate trajectory defined by, respectively, the arcuate guide member 104 or the pivot 140 together with the length of the link members 128 and 132. Of course it will be appreciated that in the case of the embodiment described above with the reference to FIG. 18A, the radius of curvature of the guide member 104 may be made infinite resulting in a linear trajectory of the tendon engaging surface as for the embodiment described above with reference to FIG. 1. However, by defining an arcuate trajectory for the tendon engaging surface 26 (with respect to the tendon engaging member 136) the latter embodiments allow a more effective, steeper, angle of attack for the bone engaging member 130 and tendon engaging member 136, improved access to the tendon through the Superior portal and, since the suture tunnel through the humerus may be also arcuate as described below, to a potentially more secure repair as increased bone material may be disposed above the sutures due to the arcuate shape of the bone tunnel curving away from the upper surface of the humerus.

In contrast to the embodiment described above with reference to FIG. 1 in which both the gap reduction and suturing operation are carried out medially of the torn tendon, the embodiments described with reference to FIG. 18 onwards are operated mostly from the lateral side. Once the tendon engaging portion has engaged the tendon and reduced the gap by advancing it against the bone engaging portion as described above, a suture channel is created from the lateral side of the torn tendon through the lateral portal.

In a first step, a first guide element having straight channels is used for guiding a drill bit to a location on the cortical bone of the humerus where it is intersected by a prolongation of the trajectory of the tendon engaging surface with respect to the bone engaging portion. Once the hard, cortical bone is pierced by the drill bit, the guide element is replaced with a second guide element having curved channels coinciding with the prolonged trajectory of the tendon engaging surface relative to the bone engaging portion (that is having the same radius of curvature and being concentric with the trajectory) to guide a curved bone piercing element such as an appropriately shaped Kirschner wire of sufficient hardness to maintain its shape while piercing through the soft cancellous bone of the humeral head. The Kirschner wire may be made from hardened stainless steel, for example with a diameter of 1 to 1.5 mm and be provided with a Trocar tip for piercing through the cancellous bone. Guided by the second guide element, the bone piercing element is advanced through the cancellous bone to reach a well-defined location at the tendon engaging surface 26.

It will be understood that in order to reach the tendon engaging surface at a well defined location independent of the angular separation between the gap reducing portion 102 and the bone engaging portion 106, the radius of curvature of the bone piercing element must be substantially the same as the radius of curvature of the trajectory of the tendon engaging surface 22 with respect to the bone engaging portion 106 whereby the curved channels of the guide member 120 ensure that the resulting pierced tunnels through the cancellous bones lie potentially in a plane defined by the gap reducing portion 102 and bone engaging portion 106.

Of course, it would be understood that if the trajectory of the tendon engaging surface is arranged to be linear, the channels of the guide member and the bone piercing element should also be of a linear configuration (in which case a bone tunnel may be drilled using a drill bit straight through to the tendon engaging surface 26 on the opposed side of the humeral head and tendon).

With reference to FIG. 26, a specific embodiment of a bone piercing assembly may include two bone piercing elements 154 such as Kirschner wires as described above joined at an end opposite their respective tips 155 by a cross member 152 such that the two bone piercing elements may be advanced through the bone simultaneously in a single operation thereby reducing the steps required for the repair. The cross member 152 maintains the other piercing elements 154 spaced at a distance corresponding to the distance between the channels 126 of the guide member 120.

As described above, the repair may include debriding the bone at the attachment site of the tendon to facilitate the attachment of the tendon. Equally, debriding the bone will facilitate the exit of the bone piercing element on the medial side of the humerus head due to the local weakening or complete debriding of the cortical bone at the attachment side.

Figure 22B:
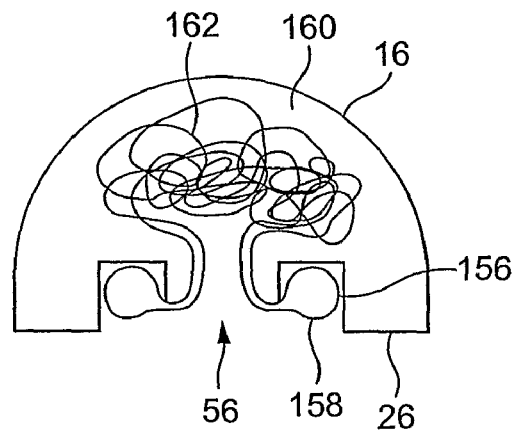

Once the tendon is reduced onto its attachment site and held in place by the tendon engaging surface 26, the repair is completed by suturing the tendon with a length of suture by passing one end through each bone channel and securing or tying the suture on the lateral aspect of the humerus through the lateral portal. To this end, the tendon engaging surface defines an aperture 56 (as depicted in FIG. 22A) through which the suture is retrieved medially to laterally from a lateral portal. It will be understood that the aperture 56 may correspond to the interior diameter of the hollow elongate member 16 such that the tendon elongating surface corresponds to the free surface of the member's wall. The tendon engaging surface may be substantially of the same kind as used in the embodiment described above with reference to FIGS. 1 and 3, that is barbed or patterned to ensure secure engagement with the tendon With reference to FIG. 22B depicting a cross-section through the hollow elongate member 16 in accordance with one specific embodiment, the interior of the hollow elongate member comprises a suture holding structure 156 for presenting a short length of suture 158 for engagement with a hook as described in detail below and a suture containing compartment 164 for containing the remaining length 162 of the suture.

With reference to FIG. 27B, the above-referenced hook may be formed adjacent of the tip 155 as a hook 164 formed as an overhang of a recess 166 adjacent to tip 155. As the bone piercing element(s) 154 are/is driven through the humerus and the fixated tendon, it enters the member 16 through the aperture 56 in a predefined location such that the hooks engage the short length of suture 158. Subsequently, the bone piercing element(s) 154 may be retracted taking with it the short length of suture 158 and consequently the remaining suture 162 through each of the bone tunnels left by the bone piercing elements 154 in the humerus.

The suture may be provided as a loop of suture such that a double length of suture is disposed through the bone tunnels resulting in a stronger repair or, alternatively may include a single length or pole of suture. In the latter case, the free ends of the suture may be releasably maintained by the suture presenting structure 156 to ensure that the free end is not lost from the hook 164 as the bone piercing elements 154 are retracted through the humerus while at the same time allowing the free ends to be disengaged from the structure 156 once the bone piercing elements 154 have been completely retracted through the humerus to then allow the free ends to follow through the bone tunnels thereby disposing a single length of suture through the bone tunnels.

Figure 22C:
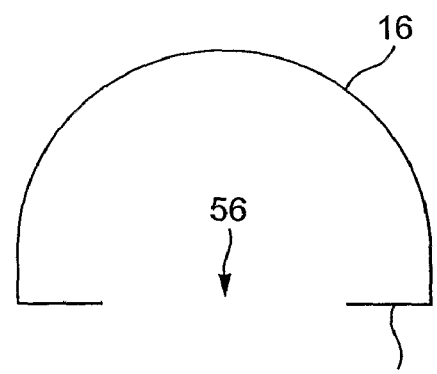

In an alternative embodiment now described with reference to FIG. 22C, the hollow member 16 is empty on the inside and defines an open end 168 (FIGS. 18A and 19) at the opposite end of the tendon engaging surface 26. With this embodiment, the corresponding bone piercing elements may define an aperture 170 adjacent to tip 155 as depicted in FIG. 27A (although a hook could equally be used). The bone piercing element is pushed on further once the tip has cleared the tendon at its attachment site to leave the body through the open end 168 to allow the sutures to be threaded through the apertures 170 by hand outside the body. The sutures may be threaded through the apertures 170 such that a single length of suture is disposed through the aperture in each of the bone piercing elements 154 and the suture may then either be tied into a loop to dispose a double length of sutures through the bone tunnels or the free ends may be left free to be retrieved through the bone tunnels as described above.

In yet a further embodiment now described with reference to FIGS. 23A and B, the tendon engaging surface 26 includes two apertures 172 linked by a channel 174 which may either be defined by a cavity inside an otherwise solid interior of the member 16 or by an appropriate channel defining structure such as a bent tube inside an otherwise hollow elongate member 16. For use with this embodiment, a bone tunnel is pre-constructed either by drilling (for an embodiment in which the repair device defines a linear trajectory for the tendon engaging surface) or Kirschner wires, as described above. Once the bone tunnels are established such that they are abutting onto the apertures 172, a single length of suture is threaded through one bone tunnel, and the channel 172 to return through the other bone tunnel. Alternatively, the suture can be daisy-chained with a suitably flexible guide wire.

Once the suture has been disposed through the bone tunnels and is free of the lateral side of the humerus it may be secured in place by tying a knot. Before the suture is secured, a suture mat may be pushed onto the sutures down to the humerus and a knot tied on top of the suture mat. The surgical skill required for the arthroscopic repair of a torn rotator cuff tendon using the repair device may further be reduced by utilising a one-way suture mat which is pushed onto the suture poles or loops and onto the humerus and allows movement of the mat along the sutures substantially only in a direction towards the humerus. Thus, the suture mat may be pushed down onto the humerus and the suture subsequently tightened without the need for a knot to be tied in order to secure the sutures.

With reference to FIGS. 25A and B, a suitable one-way suture mat has suture channels 178 with members or barbs disposed along the channel wall in an angled relationship with the channels such that a suture passing through the channel is engaged and stopped in one direction (against the angle of the barbs) and released in the other direction (with the angle of the barbs). Alternatively, a one-way toggle mechanism as described above as reference to FIG. 14 may be used on each pole or loop of the suture instead of a one-way suture mat.

Advantageously, these one-way arrangements may be passed over the sutures and onto the humerus under tension such that the sutures can be continuously tensioned until secured. This avoids the potential loss of tension when a knot or the like is tied, thereby further reducing the level of arthroscopic skill required to complete the procedure satisfactorily.

In order to provide pressure reduction or force distribution on the tendon side of the suture, the suture may be spliced to provide a spliced section 180 approximately half-way along the suture or a suture mat 182 may be slid onto the suture as shown in FIGS. 24A and B, respectively. It will be understood that this could equally be done for a loop of suture to provide a double length of suture through the bone tunnels or, alternative, a loop may be attached to each side of the spliced section 180 or the suture may 182.

The suture material, including any pressure reduction or force distribution devices, may be provided in a cartridge which is insertable into the hollow elongate member 16 and defines the suture presenting structure 156 described above with reference to FIG. 22B. The cartridge may be inserted into the member 16 through the open end 168 or through the aperture 56.

It is understood that the above description is by way of example only and that many modifications, alterations, juxtapositions and new combinations of the features described above will be derivable by a person skilled in the art. While the above embodiments have been described in relation to the repair of a torn rotator cuff, the technique and embodiments find application in the repair of other injuries where a torn tendon needs to be attached to a bone. Consequently, the scope of the invention is not limited by the above description but determined by the scope of the appended claims.

The invention claimed is:

1. A tendon repair assembly for fixing a torn tendon to an attachment site on a bone, comprising:
    a bone engaging portion for engaging a portion of bone opposite the attachment site;
    a gap reducing portion comprising a hollow elongate portion including a tendon engaging member at one end defining a tendon engaging surface for pushing the tendon onto its attachment site;
    a first guide member for linking the bone engaging portion to the gap reducing portion, the bone engaging portion and the gap reducing portion being movable with respect to each other such that, in use, the tendon can be pushed onto the attachment site by the gap reducing portion while the bone engaging portion remains engaged with the portion of bone;
    a suture cartridge insertable into the hollow elongate portion to present a suture at the tendon engaging surface; and
    a bone piercing tool having two bone piercing elements, each bone piercing element having a hook formed therein adjacent to its tip;
    wherein the bone engaging portion includes a second guide member defining two parallel channels for guiding the two bone piercing elements in a direction towards the tendon engaging surface to engage the suture with their respective hooks.

2. A tendon repair assembly as claimed in claim 1, adapted for arthroscopic repair of a rotator cuff.

3. A tendon repair assembly as claimed in claim 2 in which the tendon engaging member is arranged to be deployed through a superior portal and the bone engaging portion is arranged to be deployed through a lateral portal.

4. A tendon repair assembly as claimed in claim 1, wherein the guide member is attached to one of the gap reducing portion and the bone engaging portions and a drive mechanism is attached to the other portion of the gap reducing portion and the bone engaging portion for driving the other portion along the guide member.

5. A tendon repair assembly as claimed in claim 1 in which the assembly is arranged to guide the tendon engaging surface on an arcuate trajectory with respect to the bone engaging portion.

6. A tendon repair assembly as claimed in claim 5 in which the assembly includes a pivot linking the gap reducing portion and the bone engaging portion.

7. A tendon repair assembly as claimed in claim 6 in which the gap reducing and bone engaging portions extend on a side of the pivot opposite the tendon engaging surface to define a forceps-like arrangement.

8. A tendon repair surface as claimed in claim 1 in which the tendon engaging surface is arranged to move on a trajectory with respect to the bone engaging portion and the surface is tilted with respect to the trajectory to allow the tendon to be pushed onto and along the attachment site.

9. A tendon repair assembly as claimed in claim 1 in which the bone engaging portion includes a bone engaging member for contacting a portion of bone opposite the attachment site at one end thereof.

10. A tendon repair assembly as claimed in claim 9 in which the bone engaging member includes a single spike for contacting the portion of bone.

11. A tendon repair assembly as claimed in claim 1 in which the two channels substantially coincide with a trajectory of the tendon engaging surface with respect to the bone engaging portion thereby allowing the two channels to guide the bone piercing elements towards the tendon engaging surface.

12. A tendon repair assembly as claimed in claim 1 in which the assembly includes a one-way clutch for allowing movement of the gap reducing portion with respect to the bone engaging portion in one direction and to releasably block movement of the gap reducing portion with respect to the bone engaging portion in an opposed direction.

13. A tendon repair assembly as claimed in claim 1 in which the hollow elongate member has an open free end opposite the tendon engaging surface and in which the tendon engaging surface defines an aperture therein, thereby enabling access to the outside of the tendon engaging portion through the aperture and the open end.

14. A tendon repair assembly as claimed in claim 1, further comprising a tendon engaging member defining a longitudinal axis and the tendon engaging surface tilted with respect to the longitudinal axis and defining an aperture, the tendon engaging surface being barbed to ensure secure engagement with a tendon; and the tendon engaging member including a suture compartment containing suture materials, the suture compartment being arranged to present a suture at the tendon engaging surface such that it can be retrieved by retracting a hook through the aperture.

15. A tendon repair assembly as claimed in claim 14, wherein the tendon engaging member includes the hollow elongate portion, wherein the suture compartment includes the suture cartridge containing suture which is inserted into the hollow elongate portion.

16. A tendon repair assembly as claimed in claim 15 in which the suture includes a loop of suture.

17. A tendon repair assembly as claimed in claim 15 in which the suture includes a pressure reduction device.

18. A tendon repair assembly as claimed in claim 17 in which the suture is spliced to provide the pressure reduction device.

19. A tendon repair assembly as claimed in claim 18 in which the pressure reduction device includes a suture mat attached to the suture.

20. A tendon repair assembly as claimed in claim 1, further comprising a bone piercing assembly including the two bone piercing elements, wherein the bone piercing elements are elongated for extending through the pair of parallel channels formed in bone, each bone piercing element having a tip at one end thereof and a suture retaining structure adjacent the tip, the bone piercing elements being joined at an end opposite the tip by a cross-member.

21. A tendon repair assembly as claimed in claim 1 further comprising a ratchet mechanism arranged to releasably engage the gap reducing portion to prevent movement of the gap reducing portion away from the bone engaging portion.

22. A tendon repair assembly as claimed in claim 1 adapted for arthroscopic repair of a rotator cuff, in which the first guide member is attached to the bone engaging portion by a neck portion which is adapted such that, in use, the bone engaging portion and the gap reducing portion are deployed through separate portals.

* * * * *